United States Patent [19]

Chang

[11] Patent Number: 5,393,298
[45] Date of Patent: Feb. 28, 1995

[54] STEERING WHEEL COVER

[76] Inventor: Yih-Jong Chang, P.O. Box 82-144, Taipei, Taiwan, Prov. of China

[21] Appl. No.: 208,567

[22] Filed: Mar. 10, 1994

Related U.S. Application Data

[63] Continuation-in-part of Ser. No. 706,383, Aug. 18, 1992, Pat. No. 5,139,014.

[51] Int. Cl.⁶ .......................................... A61H 15/00
[52] U.S. Cl. .................................. 601/134; 601/136; 601/18; 601/118
[58] Field of Search ............... 601/136, 137, 143, 148, 601/134, 135, 15, 18, 19, 118, 119, 120; 74/558, 558.5, 552

[56] References Cited

U.S. PATENT DOCUMENTS

| | | | |
|---|---|---|---|
| 3,530,739 | 4/1969 | Meier | 74/558.5 |
| 4,052,982 | 10/1977 | Ozeryansky | 601/136 |
| 5,085,098 | 2/1992 | Buckley | 74/558 |
| 5,139,014 | 8/1992 | Chang | 601/19 |
| 5,213,007 | 5/1993 | Yoo | 74/558 |
| 5,224,397 | 7/1993 | Yoo | 74/558 |

Primary Examiner—Robert A. Hafer
Assistant Examiner—David J. Kenealy
Attorney, Agent, or Firm—Alfred Lei

[57] ABSTRACT

A massage steering wheel cover including a rubber ring, a plurality of massage members secured on the rubber ring and having a recess and a convex portion at both sides of the recess, the convex portion being adapted to the rubber ring to form an air chamber therebetween, the recess being provided with a plurality of round-headed protuberances, the convex portion being formed with a plurality of protuberances and a plurality of perforations, a plurality of magnets fitted into a certain number of the protuberances of the massage member, and a plurality of leather members secured on the rubber ring.

3 Claims, 4 Drawing Sheets

STEERING WHEEL COVER

CROSS-REFERENCE

This application is a continuation-in-part of the U.S. Ser. No. 706,383, now U.S. Pat. No. 5,139,014, issued on Aug. 18, 1992.

BACKGROUND OF THE INVENTION

It has been found that conventional steering wheel cover is simply made of leather and does not have any other function than increasing the frictional coefficient between the driver's hand and the steering wheel. Hence, the inventor has devoted himself to designing a steering wheel cover which has many purposes in addition to enhancing the safety of driving.

Therefore, it is an object of the present invention to provide a steering wheel cover which can make the driver recover from tiredness, provide the driver with magnetic therapy, and keep the hands of the driver dried.

SUMMARY OF THE INVENTION

This invention relates to a novel steering wheel cover.

It is the primary object of the present invention to provide a novel steering wheel cover which may massage the hands of a driver and and provide him with magnetic therapy.

It is another object of the present invention to provide a novel steering wheel cover which can help the driver grasp a steering wheel firmly.

It is another object of the present invention to provide a novel steering wheel cover which can keep the hands of a driver dried.

It is still another object of the present invention to provide a novel steering wheel cover which can make the driver recover from tiredness.

It is a further object of the present invention to provide a novel steering wheel cover which is economical to manufacture.

Other objects and merits and a fuller understanding of the present invention will be obtained by those having ordinary skill in the art when the following detailed description of the preferred embodiment is read in conjunction with the accompanying drawings wherein like numerals refer to like or similar parts.

DETAILED DESCRIPTION OF THE PREFERRED EMBODIMENT

Figure 1:
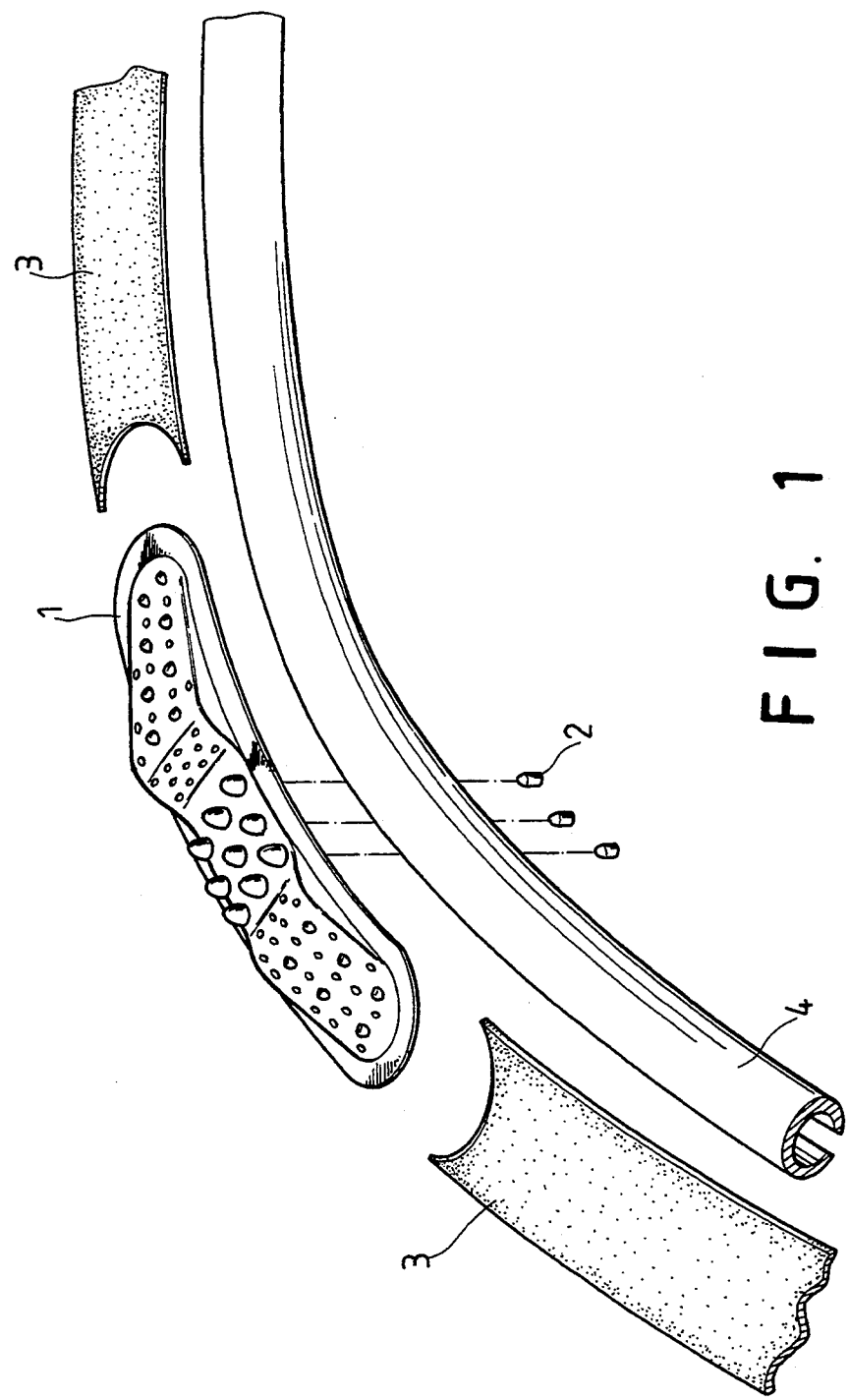
FIG. 1 is an exploded view of the present invention.

For purpose of promoting an understanding of the principles of the invention, reference will now be made to the embodiment illustrated in the drawings. Specific language will be used to describe same. It will, nevertheless, be understood that no limitation of the scope of the invention is thereby intended, such alternations and further modifications in the illustrated device, and such further applications of the principles of the invention as illustrated herein being contemplated as would normally occur to one skilled in the art to which the invention relates.

Figure 2:
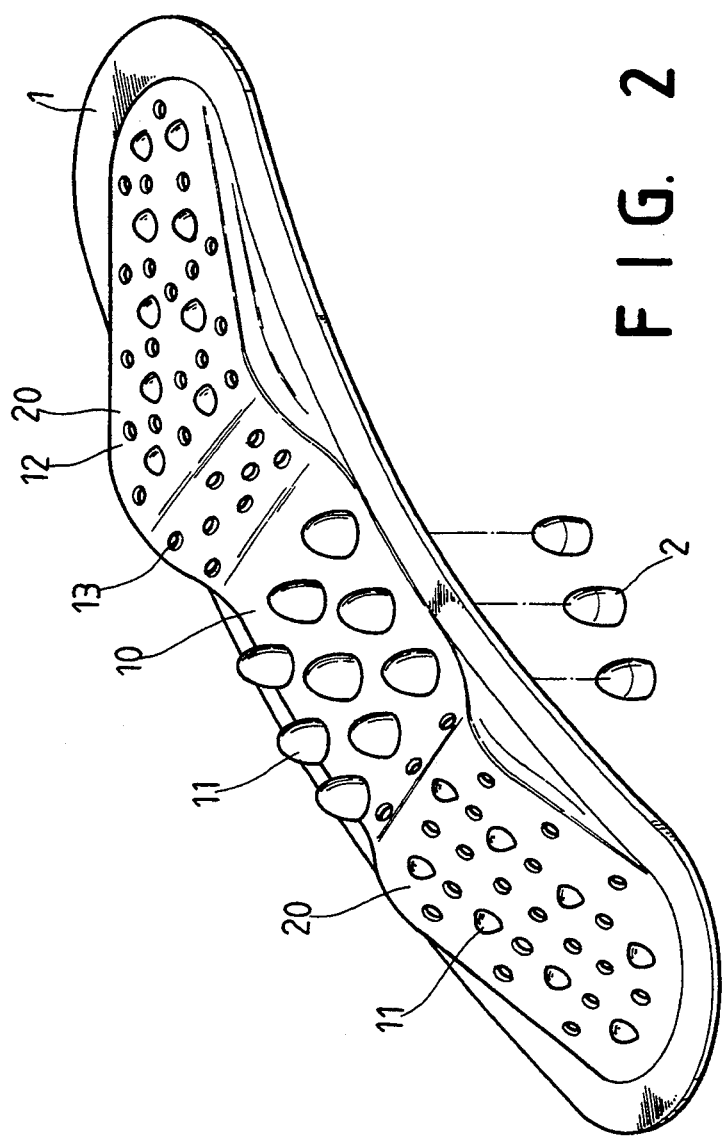
FIG. 2 is a perspective view of the massage member.
Figure 3:
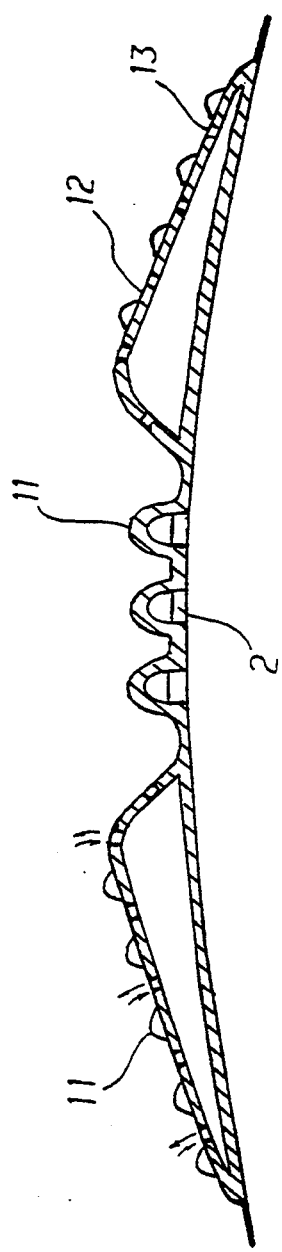
FIG. 3 is a sectional view of the massage member.
Figure 4:
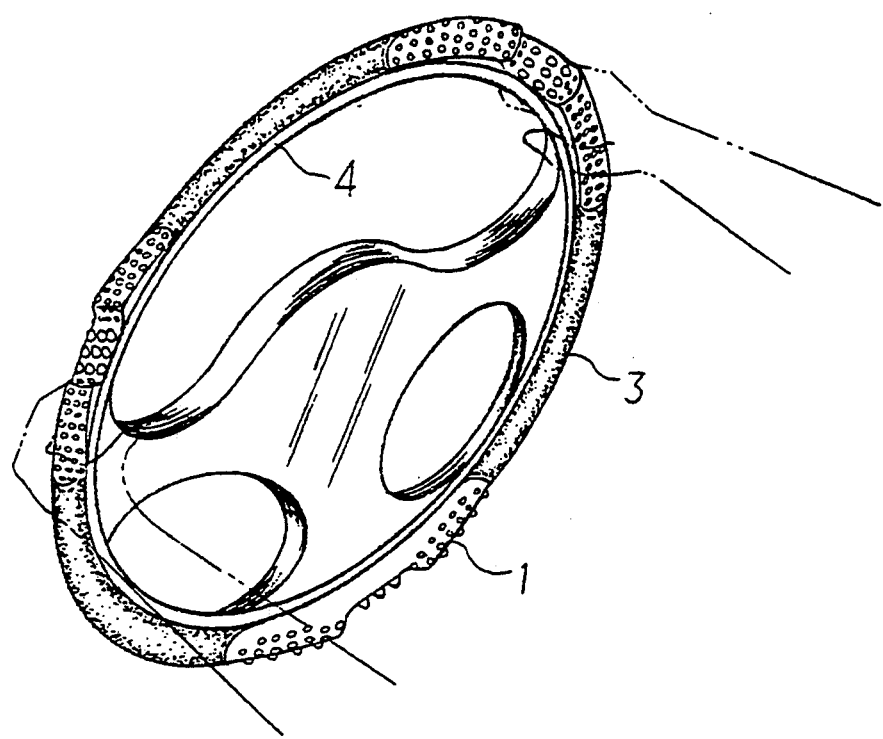
FIG. 4 is a working view of the present invention.

With reference to the drawings and in particular to FIGS. 1 and 2 thereof, the steering wheel cover according to the present invention mainly comprises a plurality of massage members 1, a plurality of leather members 3, and a rubber ring 4. The massage member 1 is formed with a recess 10 and a convex portion 20 at both sides of the recess 10. The recess 10 is provided with a plurality of round-headed protuberances 11. The convex portion 20 is formed with a plurality of protuberances 11 and perforations 13. In each of the protuberances 11 of the massage member 1 is fitted a magnet 2. The massage members 1 and the leather members 3 are alternately secured on the rubber ring 4 (see FIG. 4). The convex portions 20 of the massage member 1 are adapted to the rubber ring 4 to form an air chamber therebetween. Further, the convex portions 20 of the massage member 1 may be provided with a closed bottom.

As the convex portion 3 of the massage member 1 is compressed and released, the air stored therein will be pumped out of the perforations 13 thereby drying the hand of the driver. In the meantime, the round-headed protuberance 11 of the massage member 1 will continuously emit magnetic lines from the North pole to the South pole so that when the driver's hand is in contact with the round-headed protuberance, the veins and vital points of the body will be appropriately stimulated hence achieving the purpose of massage. Moreover, the magnetic lines of force will promote the blood circulation as well as metabolism thereby making the driver recover from tiredness.

The invention is naturally not limited in any sense to the particular features specified in the forgoing or to the details of the particular embodiment which has been chosen in order to illustrate the invention. Consideration can be given to all kinds of variants of the particular embodiment which has been described by way of example and of its constituent elements without thereby departing from the scope of the invention. This invention accordingly includes all the means constituting technical equivalents of the means described as well as their combinations.

I claim:

1. A massage steering wheel cover comprising:
a rubber ring;
a plurality of massage members secured on said rubber ring, each of said massage members having a recess at an intermediate portion and a convex portion at both sides of said recess, said convex portion being formed with a plurality of protuberances and a plurality of perforations and being adhered to said rubber ring to form an air chamber therebetween, said recess being provided with a plurality of round-headed protuberances;
a plurality of leather members secured on said rubber ring;
said massage members and said leather members being alternatively secured on said rubber ring.

2. The massage steering wheel cover as claimed in claim 1, further comprising a plurality of magnets fitted into at least one of the protuberances of said massage members.

3. The massage steering wheel cover as claimed in claim 1, wherein the convex portion of said massage members is provided with a closed bottom.

* * * * *